United States Patent [19]
Nabika et al.

[11] Patent Number: 6,136,995
[45] Date of Patent: Oct. 24, 2000

[54] PROCESS FOR PRODUCING AMINOSILANE COMPOUNDS

[75] Inventors: Masaaki Nabika, Ichihara; Kotohiro Nomura, Ikoma, both of Japan

[73] Assignee: Sumitomo Chemical Company, Limited, Osaka, Japan

[21] Appl. No.: 09/186,880

[22] Filed: Nov. 6, 1998

[30] Foreign Application Priority Data

Nov. 7, 1997 [JP] Japan .................................... 9-305364

[51] Int. Cl.⁷ ...................................................... C07R 7/10
[52] U.S. Cl. ............................................................ 556/413
[58] Field of Search ............................................. 556/413

[56] References Cited

U.S. PATENT DOCUMENTS

| | | |
|---|---|---|
| 5,055,438 | 10/1991 | Canich . |
| 5,168,111 | 12/1992 | Canich . |
| 5,254,707 | 10/1993 | Strickler et al. ........................ 556/413 |
| 5,453,221 | 9/1995 | Lisowsky ................................ 556/413 |
| 5,476,716 | 12/1995 | Lisowsky ................................ 556/413 |
| 5,591,879 | 1/1997 | Frey et al. .............................. 556/413 |
| 5,703,187 | 12/1997 | Timmers . |
| 5,831,106 | 11/1998 | Langhauser et al. .................. 556/413 |

FOREIGN PATENT DOCUMENTS

| | | |
|---|---|---|
| 7-053618 | 2/1995 | Japan . |
| 5-505593 | 9/1996 | Japan . |
| 8-239412 | 9/1996 | Japan . |
| WO 93/08199A1 | 4/1993 | WIPO . |
| WO 93/08221A2 | 4/1993 | WIPO . |

*Primary Examiner*—Paul F. Shaver
*Attorney, Agent, or Firm*—Birch, Stewart, Kolasch & Birch, LLP

[57] ABSTRACT

The present invention provides a process for producing aminosaline compounds which are useful as precursors for ligands in the transition metal complexes, said process avoiding handling of solid which is troublesome in isolation and purification and combustible upon contact with air, having smaller number of reaction steps, and giving a high yield, in industrial scale. The present invention has a great value that said process for production could be carried out at an industrially advantageous temperature of −20° or higher.

11 Claims, No Drawings

PROCESS FOR PRODUCING AMINOSILANE COMPOUNDS

BACKGROUND OF THE INVENTION

1. Field of the Invention

The present invention relates to a process for producing a specific aminosilane compound, which is effective particularly in industrial production.

2. Description of the Related Arts

Aminosilane compounds containing a group having a cyclopentadiene skeleton are recently attractive as ligands for various transition metal complexes, or the like. The transition metal complexes having these ligands are effective in many reactions for organic synthesis. Among them, specific complexes of early transition metals such as titanium, zirconium or the like are extremely effective as components for olefin polymerization of olefins and are being widely studied including their practical application. (e.g. WO 93/08199, U.S. Pat. No. 5,096,867).

Synthesis of these aminosilane compounds containing a group having a cyclopentadiene skeleton is usually conducted by a three-step reaction in which respective starting compounds for three parts (i.e., a part for a group having a cyclopentadiene skeleton, a part for an amino group and a part for a silane skeleton) of these compounds are joined together. Thus, they are usually synthesized by first reacting a compound having a cyclopentadiene skeleton with an organic alkali metal compound such as methyl lithium, n-butyl lithium or the like in the presence of a solvent such as hexane or the like to synthesize an alkali metal salt of the compound having a cyclopentadiene skeleton, removing an excess organic alkali metal compound by isolation by filtration/drying, and then reacting the salt with a chlorinated silyl compound, further reacting the isolated reaction product with an amine or its alkali metal salt (e.g. JP-A-7-53618, JP-A-5-505593, WO 93/08221) The yield in the conventionally known synthetic process, however, is not completely satisfactory.

The process in which a compound having a cyclopentadiene skeleton is reacted with an organic alkali metal compound such as methyl lithium, n-butyl lithium or the like synthesize an alkali metal salt of the compound having a cyclopentadiene skeleton is generally performed by a process described by C. M. Fendrick et al. In Organometallics, No. 3, page 819 (1984) or others, and uses as a solvent hexane or the like which is a solvent for commercially available organic alkali metal compounds.

Generally, the alkali metal salts of the compound having a cyclopentadiene skeleton are very sensitive to the air. Therefore, industrial performance of isolation treatment for the alkali metal salts of the compound having a cyclopentadiene skeleton had a considerable number of problems such as combustion by contacting with air, difficulty of stirring in the reaction system without the large amount of solvent and extreme decrease in filtering efficiency, due to a great increase in volume in the aliphatic solvent such as hexane and the like.

In addition, while the synthesis of the alkali metal salts of the compound having a cyclopentadiene skeleton has been carried out at a temperature of about −78° C. in a laboratory scale in many cases, the reaction in the industrial scale at a low temperature at about −78° C. requires much economical burden. Furthermore, there are many restrictions for the apparatus to be used and quality thereof. Therefore, a need exists for the establishment of a reaction technique that allows the performance of the reaction at an industrially advantageous temperature range of −20° C. or above.

SUMMARY OF THE INVENTION

An object of the present invention is to provide a process for producing aminosilane compounds which are useful as precursors for ligands in the transition metal complexes, without handling of solid which is troublesome in isolation and purification and combustible upon contact with air, the said process having smaller number of reaction steps and giving a high yield.

Another object of the present invention is to provide a process for producing the above aminosilane compounds, said process being capable of being carried out at an industrially advantageous reaction temperature.

The present invention provides a process for producing an aminosilane compound represented by the general formula (1) described below, which comprises successively carrying out steps (A), (B) and (C) in this order without an intervening isolation nor purification treatment:

Step (A): a step for reacting a compound having a cyclopentadiene skeleton with a strong base;

Step (B): a step for reacting the reaction product obtained in the step (A) with a silane compound represented by the general formula (2); and Step (C): a step for reacting the reaction product obtained in the step (B) with an amine compound represented by the general formula (3) or an alkali metal amide compound represented by the general formula (4);

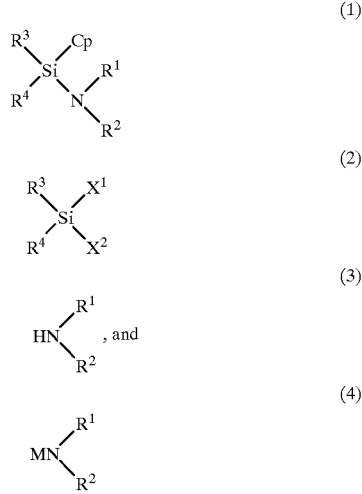

(wherein, Cp is a group having a cyclopentadiene skeleton, and M is an alkali metal atom; $R^1$ and $R^2$ independently represent a hydrogen atom, an alkyl group, an aralkyl group, an aryl group or a substituted silyl group; $R^3$ and $R^4$ independently represent an alkyl group, an aralkyl group, an aryl group, a substituted silyl group, an alkoxy group, an aralkyloxy group or an aryloxy group; in addition, ($R^1$ and $R^2$) and/or ($R^3$ and $R^4$) may be linked to each other to form a ring; and $X^1$ and $X^2$ independently represent a halogen atom.)

DETAILED DESCRIPTION OF THE INVENTION

The present invention will be explained below in more detail.

In the aminosilane compound represented by the general formula (1) described above, Cp is a group having a cyclopentadiene skeleton and includes a cyclopentadienyl group, indenyl group, fluorenyl group or the like which may be substituted with an alkyl group having 1 to 20 carbon atoms, an aryl group having 6 to 20 carbon atoms, an aralkyl group having 7 to 20 carbon atoms, a substituted silyl group having 1 to 20 carbon atoms, an alkoxy group having 1 to 20 carbon atoms, an aryloxy group having 6 to 20 carbon atoms or an aralkyloxy group having 7 to 20 carbon atoms.

Specific examples include cyclopentadienyl group, methylcyclopentadienyl group, dimethylcyclopentadienyl group, trimethylcyclopentadienyl group, tetramethylcyclopentadienyl group, ethylcyclopentadienyl group, n-propylcyclopentadienyl group, isopropylcyclopentadienyl group, n-butylcyclopentadienyl group, sec-butylcyclopentadienyl group, tert-butylcyclopentadienyl group, n-pentylcyclopentadienyl group, neopentylcyclopentadienyl group, n-hexylcyclopentadienyl group, n-octylcyclopentadienyl group, phenylcyclopentadienyl group, naphthylcyclopentadienyl group, trimethylsilylcyclopentadienyl group, triethylsilylcyclopentadienyl group, tert-butyldimethylsilylcyclopentadienyl group, diethylcyclopentadienyl group, di-n-propylcyclopentadienyl group, diisopropylcyclopentadienyl group, di-n-butylcyclopentadienyl group, di-sec-butylcyclopentadienyl group, di-tert-butylcyclopentadienyl group, di-n-pentylcyclopentadienyl group, dineopentylcyclopentadienyl group, di-n-hexylcyclopentadienyl group, di-n-octylcyclopentadienyl group, diphenylcyclopentadienyl group, dinaphthylcyclopentadienyl group, di-(trimethylsilyl)-cyclopentadienyl group, di-(triethylsilyl)-cyclopentadienyl group, di-(tert-butyldimethylsilyl)-cyclopentadienyl group, triethylcyclopentadienyl group, tri-n-propylcyclopentadienyl group, triisopropylcyclopentadienyl group, tri-n-butylcyclopentadienyl group, tri-sec-butylcyclopentadienyl group, tri-tert-butylcyclopentadienyl group, tri-n-pentylcyclopentadienyl group, trineopentylcyclopentadienyl group, tri-n-hexylcyclopentadienyl group, tri-n-octylcyclopentadienyl group, tri-(trimethylsilyl)-cyclopentadienyl group, tri-(triethylsilyl)-cyclopentadienyl group, tri-(tert-butyldimethylsilyl)-cyclopentadienyl group, 1-indenyl group, 4,5,6,7-tetrahydro-1-indenyl group, 9-fluorenyl group and the like.

Preferably, Cp is a group having a cyclopentadiene skeleton carrying at least one substituent on its five-membered ring, and more preferably, Cp is a group having a cyclopentadiene skeleton carrying at least two substituents on its five-membered ring. A particularly preferred substituent in this case is an alkyl group having 1 to 20 carbon atoms or a substituted silyl group having 1 to 20 carbon atoms.

The most preferred Cp in the compound applied in the present invention is a tetramethylcyclopentadienyl group, a dimethylcyclopentadienyl group, a di-tert-butylcyclopentadienyl group, an diisopropylcyclopentadienyl group, or an isopropyl-tert-butylcyclopentadienyl group.

Plural isomers may exist due to the difference of the position of substituents at the cyclopentadiene skeleton in the substituted Cp or the difference of the position of the double bonds, but it should be appreciated that all the isomers are included in the scope of the present invention.

In the general formula (1), $R^1$ and $R^2$ independently are a hydrogen atom, an alkyl group, an aralkyl group, an aryl group or a substituted silyl group, and preferably a hydrogen atom, an alkyl group having 1 to 20 carbon atoms, an aralkyl group having 7 to 20 carbon atoms, an aryl group having 6 to 20 carbon atoms or a substituted silyl group having 1 to 20 carbon atoms.

Specific examples of the alkyl group in $R^1$ and $R^2$ include, for example, methyl group, ethyl group, n-propyl group, isopropyl group, n-butyl group, sec-butyl group, tert-butyl group, n-pentyl group, neopentyl group, isopentyl group, n-hexyl group, n-octyl group, n-decyl group, n-dodecyl group, n-pentadecyl group, n-eicosyl group and the like. Preferred examples include methyl group, ethyl group, isopropyl group, tert-butyl group, n-pentyl group, neopentyl group or isopentyl group.

These alkyl groups may respectively be substituted with a halogen atom such as fluorine atom, chlorine atom, bromine atom or iodine atom; alkoxy group such as methoxy group, ethoxy group or the like; aralkyloxy group such as benzyloxy group or the like, aryloxy group such as phenoxy group or the like; or the like.

The alkyl group having 1 to 20 carbon atoms and substituted with a halogen atom includes, for example, fluoromethyl group, difluoromethyl group, trifluoromethyl group, chloromethyl group, dichloromethyl group, trichloromethyl group, bromoomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromooethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicocyl group, perchloropropyl group, perchlorobutyl group, perchloropentyl group, perchlorohexyl group, perchlorooctyl group, perchlorododecyl group, perchloropentadecyl group, perchloroeicocyl group, perbromopropyl group, perbromobutyl group, perbromopentyl group, perbromohexyl group, perbromooctyl group, perbromododecyl group, perbromopentadecyl group, perbromoeicocyl group and the like.

Specific examples of the aralkyl group in $R^1$ and $R^2$ of the general formula (1) include, for example, benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, (n-tetradecylphenyl)methyl group, naphthylmethyl group, anthracenylmethyl group and the like, preferably benzyl group.

These aralkyl groups may respectively be substituted with a halogen atom such as fluorine atom, chlorine atom, bromine atom or iodine atom; alkoxy group such as methoxy group, ethoxy group or the like; aralkyloxy group such as benzyloxy group or the like, aryloxy group such as phenoxy group or the like; or the like.

Specific examples of the aryl group in $R^1$ and $R^2$ of the general formula (1) include, for example, phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group and the like, preferably phenyl group.

These aryl groups may respectively be substituted with a halogen atom such as fluorine atom, chlorine atom, bromine atom or iodine atom; alkoxy group such as methoxy group, ethoxy group or the like; aralkyloxy group such as benzyloxy group or the like, aryloxy group such as phenoxy group or the like; or the like.

The substituted silyl group in $R^1$ and $R^2$ of the general formula (1) is preferably a silyl group substituted with a hydrocarbon group. The hydrocarbon group include, for example, alkyl groups having 1 to 10 carbon atoms such as methyl group, ethyl group, n-propyl group, isopropyl group, n-butyl group, sec-butyl group, tert-butyl group, isobutyl group, n-pentyl group, n-hexyl group, cyclohexyl group and the like; and aryl groups such as phenyl group and the like. Examples of the substituted silyl group having 1 to 20 carbon atoms include mono-substituted silyl group having 1 to 20 carbon atoms, such as methylsilyl group, ethylsilyl group, phenylsilyl group and the like; di-substituted silyl group having 2 to 20 carbon atoms, such as dimethylsilyl group, diethylsilyl group, diphenylsilyl group and the like; tri-substituted silyl group having 3 to 20 carbon atoms, such as trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyl-dimethylsilyl group, tri-n-pentylsilyl group, tri-n-hexylsilyl group, tricyclohexylsilyl group, triphenylsilyl group and the like; preferably trimethylsilyl group, tert-butyldimethylsilyl group, or triphenylsilyl group.

These substituted silyl groups may respectively be substituted with a halogen atom such as fluorine atom, chlorine atom, bromine atom or iodine atom; alkoxy group such as methoxy group, ethoxy group or the like; aralkyloxy group such as benzyloxy group or the like, aryloxy group such as phenoxy group or the like; or the like.

The substituents $R^1$ and $R^2$ in the general formula (1) may optionally be linked to each other to form a ring.

The substituents $R^1$ and $R^2$ in the general formula (1) preferably independently represent a hydrogen atom, an alkyl group having 1 to 20 carbon atoms, or a substituted silyl group having 1 to 20 carbon atoms. For the most preferred $R^1$ and $R^2$ applied to the present invention, one of $R^1$ and $R^2$ is a hydrogen atom and the other is the alkyl group or the substituted silyl group.

In the general formula (1), $R^3$ and $R^4$ independently represent an alkyl group, aryl group, a substituted silyl group, alkoxy group, aralkyloxy group, or aryloxy group, preferably an alkyl group having 1 to 20 carbon atoms, an aralkyl group having 7 to 20 carbon atoms, an aryl group having 6 to 20 carbon atoms or a substituted silyl group having 1 to 20 carbon atoms, an alkoxy group having 1 to 20 carbon atoms, an aralkyloxy group having 7 to 20 carbon atoms or an aryloxy group having 6 to 20 carbon atoms. In addition, $R^3$ and $R^4$ may be linked to form a ring.

The alkyl group, the aralkyl group, the aryl group, and the substituted silyl group as $R^3$ and $R^4$ are the same as those described above for $R^1$ and $R^2$.

The alkoxy group in $R^3$ and $R^4$ of the general formula (1) is preferably an alkoxy group having 1 to 20 carbon atoms, and includes, for example, methoxy group, ethoxy group, n-propoxy group, isopropoxy group, n-butoxy group, sec-butoxy group, tert-butoxy group, n-pentyloxy group, neopentyloxy group, n-hexyloxy group, n-octyloxy group, n-dodecyloxy group, n-pentadecyloxy group, n-eicosyloxy group and the like. Preferred examples include methoxy group, ethoxy group and tert-butoxy group.

These alkoxy groups may respectively be substituted with a halogen atom such as fluorine atom, chlorine atom, bromine atom or iodine atom; alkoxy group such as methoxy group, ethoxy group or the like; aralkyloxy group such as benzyloxy group or the like, aryloxy group such as phenoxy group or the like; or the like.

The aralkyloxy group in $R^3$ and $R^4$ of the general formula (1) is preferably an aralkyloxy group having 7 to 20 carbon atoms, and includes, for example, benzyloxy group, (2-methylphenyl)methoxy group, (3-methylphenyl)methoxy group, (4-methylphenyl)methoxy group, (2,3-dimethylphenyl)methoxy group, (2,4-dimethylphenyl) methoxy group, (2,5-dimethylphenyl)methoxy group, (2,6-dimethylphenyl)methoxy group, (3,4-dimethylphenyl) methoxy group, (3,5-dimethylphenyl)methoxy group, (2,3,4-trimethylphenyl)methoxy group, (2,3,5-trimethylphenyl) methoxy group, (2,3,6-trimethylphenyl)methoxy group, (2,4,5-trimethylphenyl)methoxy group, (2,4,6-trimethylphenyl)methoxy group, (3,4,5-trimethylphenyl) methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl) methoxy group, (ethylphenyl)methoxy group, (n-propylphenyl)methoxy group, (isopropylphenyl)methoxy group, (n-butylphenyl)methoxy group, (sec-butylphenyl) methoxy group, (tert-butylphenyl)methoxy group, (n-hexylphenyl)methoxy group, (n-octylphenyl)methoxy group, (n-decylphenyl)methoxy group, (n-tetradecylphenyl) methoxy group, naphthylmethoxy group, anthracenyl-methoxy group and the like, preferably benzyloxy group.

These aralkyloxy groups may respectively be substituted with a halogen atom such as fluorine atom, chlorine atom, bromine atom or iodine atom; alkoxy group such as methoxy group, ethoxy group or the like; aralkyloxy group such as benzyloxy group or the like, aryloxy group such as phenoxy group or the like; or the like.

The aryloxy group in $R^3$ and $R^4$ of the general formula (1) is preferably an aryloxy group having 6 to 20 carbon atoms, and includes, for example, phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group, anthracenoxy group and the like.

These aryloxy groups may respectively be substituted with a halogen atom such as fluorine atom, chlorine atom, bromine atom or iodine atom; alkoxy group such as methoxy group, ethoxy group or the like; aralkyloxy group such as benzyloxy group or the like, aryloxy group such as phenoxy group or the like; or the like.

The $R^3$ and $R^4$ may be linked to each other to form a ring.

The substituents $R^3$ and $R^4$ are preferably and independently the alkyl group or the aryl group.

Specific examples of the aminosilane compound of the general formula (1) include (tetramethylcyclopentadienyl)(tert-butylamino) dimethylsilane, (tetramethylcyclopentadienyl)(cyclohexylamino) dimethylsilane, (tetramethylcyclopentadienyl) (phenylamino) dimethylsilane, (tetramethylcyclopentadienyl)(N-trimethylsilyl-amino)dimethylsilane, (tetramethylcyclopentadienyl)(tert-butylamino) diphenylsilane, (tetramethylcyclopentadienyl)(cyclohexylamino) diphenylsilane, (tetramethylcyclopentadienyl) (phenylamino) diphenylsilane, (tetramethylcyclopentadienyl)(N-trimethylsilylamino) diphenylsilane, (tetramethylcyclopentadienyl)(tert-butylamino) methylphenylsilane, (tetramethylcyclopentadienyl)(cyclohexylamino) methylphenylsilane, (tetramethylcyclopentadienyl)(phenylamino) methylphenylsilane, (tetramethylcyclopentadienyl)(N-trimethylsilylamino)methylphenylsilane, (cyclopentadienyl)(tert-butylamino)dimethylsilane, (cyclopentadienyl)(cyclohexylamino)dimethylsilane, (cyclopentadienyl)(phenylamino)dimethylsilane, (cyclopentadienyl)(N-trimethylsilylamino) dimethylsilane, (cyclopentadienyl)(tert-butylamino) diphenylsilane, (cyclopentadienyl)(cyclohexylamino) diphenylsilane, (cyclopentadienyl)(phenylamino) diphenylsilane, (cyclopentadienyl)(N-trimethylsilylamino)diphenylsilane, (cyclopentadienyl)(tert-butylamino)methylphenylsilane, (cyclopentadienyl)(cyclohexylamino) methylphenylsilane, (cyclopentadienyl)(phenylamino) methylphenylsilane, (cyclopentadienyl)(N-trimethylsilylamino) methylphenylsilane, (methylcyclopentadienyl)(tert-butylamino) dimethylsilane, (methylcyclopentadienyl)(cyclohexylamino) dimethylsilane, (methylcyclopentadienyl) (phenylamino) dimethylsilane, (methylcyclopentadienyl)(N-trimethylsilylamino) dimethylsilane, (methylcyclopentadienyl)(tert-butylamino) diphenylsilane, (methylcyclopentadienyl)(cyclohexylamino)diphenylsilane, (methylcyclopentadienyl)(phenylamino) diphenylsilane, (methylcyclopentadienyl)(N-trimethylsilylamino) diphenylsilane, (methylcyclopentadienyl)(tert-butylamino) methylphenylsilane, (methylcyclopentadienyl) (cyclohexylamino)methylphenylsilane, (methylcyclopentadienyl)(phenylamino) methylphenylsilane, (methylcyclopentadienyl)(N-trimethylsilylamino)methylphenylsilane, (isopropylcyclopentadienyl)(tert-butylamino) dimethylsilane, (isopropylcyclopentadienyl)(cyclohexylamino) dimethylsilane, (isopropylcyclopentadienyl) (phenylamino) dimethylsilane, (isopropylcyclopentadienyl)(N-trimethylsilylamino)dimethylsilane, (isopropylcyclopentadienyl)(tert-butylamino) diphenylsilane, (isopropylcyclopentadienyl)(cyclohexylamino) diphenylsilane, (isopropylcyclopentadienyl) (phenylamino) diphenylsilane, (isopropylcyclopentadienyl)(N-trimethylsilylamino)diphenylsilane, (isopropylcyclopentadienyl)(tert-butylamino) methylphenylsilane, (isopropylcyclopentadienyl)(cyclohexylamino) methylphenylsilane, (isopropylcyclopentadienyl) (phenylamino) methylphenylsilane, (isopropylcyclopentadienyl)(N-trimethylsilylamino) methylphenylsilane, (tert-butylcyclopentadienyl)(tert-butylamino) dimethylsilane, (tert-butylcyclopentadienyl)(cyclohexylamino)dimethylsilsne, (tert-butylcyclopentadienyl)(phenylamino)dimethylsilane, (tert-butylcyclopentadienyl)(N-trimethylsilylamino) dimethylsilane, (tert-butylcyclopentadienyl)(tert-butylamino)diphenylsilane, (tert-butylcyclopentadienyl) (cyclohexylamino) diphenylsilane, (tert-butylcyclopentadienyl) (phenylamino)diphenylsilane, (tert-butylcyclopentadienyl)(N-trimethylsilylamino) diphenylsilane, (tert-butylcyclopentadienyl)(tert-butylamino)methylphenylsilane, (tert-butylcyclopentadienyl)(cyclohexylamino) methylphenylsilane, (tert-butylcyclopentadienyl) (phenylamino)methylphenylsilane, (tert-butylcyclopentadienyl)(N-trimethylsilylamino) methylphenylsilane, (n-butylcyclopentadienyl)(tert-butylamino)dimethylsilane, (n-butylcyclopentadienyl)(cyclohexylamino)dimethylsilane, (n-butylcyclopentadienyl)(phenylamino) dimethylsilane, (n-butylcyclopentadienyl)(N-trimethylsilylamino) dimethylsilane, (n-butylcyclopentadienyl)(tert-butylamino) diphenylsilane, (n-butylcyclopentadienyl)(cyclohexylamino)diphenylsilane, (n-butylcyclopentadienyl)(phenylamino) diphenylsilane, (n-butylcyclopentadienyl)(N-trimethylsilylamino) diphenylsilane, (n-butylcyclopentadienyl)(tert-butylamino) methylphenylsilane, (n-butylcyclopentadienyl)(cyclohexylamino)methylphenylsilane, (n-butylcyclopentadienyl)(phenylamino) methylphenylsilane, (n-butylcyclopentadienyl)(N-trimethylsilylamino)methylphenylsilane, (isobutylcyclopentadienyl)(tert-butylamino) dimethylsilane, (isobutylcyclopentadienyl)(cyclohexylamino)dimethylsilane, (isobutylcyclopentadienyl)(phenylamino) dimethylsilane, (isobutylcyclopentadienyl)(N-trimethylsilylamino) dimethylsilane, (isobutylcyclopentadienyl)(tert-butylamino) diphenylsilane, (isobutylcyclopentadienyl)(cyclohexylamino)diphenylsilane, (isobutylcyclopentadienyl)(phenylamino)

diphenylsilane, (isobutylcyclopentadienyl)(N-trimethylsilylamino) diphenylsilane, (isobutylcyclopentadienyl)(tert-butylamino) methylphenylsilane, (isobutylcyclopentadienyl)(cyclohexylamino)methylphenyl silane, (isobutylcyclopentadienyl)(phenylamino) methylphenylsilane, (isobutylcyclopentadienyl)(N-trimethylsilylamino)methylphenylsilane, (n-pentylcyclopentadienyl)(tert-butylamino) dimethylsilane, (n-pentylcyclopentadienyl)(cyclohexylamino)dimethylsilane, (n-pentylcyclopentadienyl)(phenylamino) dimethylsilane, (n-pentylcyclopentadienyl)(N-trimethylsilylamino) dimethylsilane, (n-pentylcyclopentadienyl)(tert-butylamino) diphenylsilane, (n-pentylcyclopentadienyl)(cyclohexylamino) diphenylsilane, (n-pentylcyclopentadienyl)(phenylamino) diphenylsilane, (n-pentylcyclopentadienyl)(N-trimethylsilylamino)diphenylsilane, (n-pentylcyclopentadienyl)(tert-butylamino) methylphenylsilane, (n-pentylcyclopentadienyl)(cyclohexylamino)methylphenylsilane, (n-pentylcyclopentadienyl)(phenylamino) methylphenylsilane, (n-pentylcyclopentadienyl)(N-trimethylsilylamino) methylphenylsilane, (neopentylcyclopentadienyl)(tert-butylamino) dimethylsilane, (neopentylcyclopentadienyl)(cyclohexylamino)dimethylsilane, (neopentylcyclopentadienyl)(phenylamino) dimethylsilane, (neopentylcyclopentadienyl)(N-trimethylsilylamino) dimethylsilane, (neopentylcyclopentadienyl)(tert-butylamino) diphenylsilane, (neopentylcyclopentadienyl)(cyclohexylamino)diphenylsilane, (neopentylcyclopentadienyl)(phenylamino) diphenylsilane, (neopentylcyclopentadienyl)(N-trimethylsilylamino) diphenylsilane, (neopentylcyclopentadienyl)(tert-butylamino) methylphenylsilane, (neopentylcyclopentadienyl)(cyclohexylamino) methylphenylsilane, (neopentylcyclopentadienyl) (phenylamino) methylphenylsilane, (neopentylcyclopentadienyl)(N-trimethylsilylamino) methylphenylsilane, (n-hexylcyclopentadienyl)(tert-butylamino) dimethylsilane, (n-hexylcyclopentadienyl)(cyclohexylamino)dimethylsilane, (n-hexylcyclopentadienyl)(phenylamino) dimethylsilane, (n-hexylcyclopentadienyl)(N-trimethylsilylamino) dimethylsilane, (n-hexylcyclopentadienyl)(tert-butylamino) diphenylsilane, (n-hexylcyclopentadienyl)(cyclohexylamino)diphenylsilane, (n-hexylcyclopentadienyl)(phenylamino) diphenylsilane, (n-hexylcyclopentadienyl)(N-trimethylsilylamino) diphenylsilane, (n-hexylcyclopentadienyl)(tert-butylamino) methylphenylsilane, (n-hexylcyclopentadienyl)(cyclohexylamino) methylphenylsilane, (n-hexylcyclopentadienyl) (phenylamino) methylphenylsilane, (n-hexylcyclopentadienyl)(N-trimethylsilylamino)methylphenylsilane, (n-octylcyclopentadienyl)(tert-butylamino) dimethylsilane, (n-octylcyclopentadienyl)(cyclohexylamino)dimethylsilane, (n-octylcyclopentadienyl)(phenylamino) dimethylsilane, (n-octylcyclopentadienyl)(N-trimethylsilylamino) dimethylsilane, (n-octylcyclopentadienyl)(tert-butylamino) diphenylsilane, (n-octylcyclopentadienyl)(cyclohexylamino)diphenylsilane, (n-octylcyclopentadienyl)(phenylamino) diphenylsilane, (n-octylcyclopentadienyl)(N-trimethylsilylamino)diphenylsilane, (n-octylcyclopentadienyl)(tert-butylamino) methylphenylsilane, (n-octylcyclopentadienyl)(cyclohexylamino) methylphenylsilane, (n-octylcyclopentadienyl) (phenylamino) methylphenylsilane, (n-octylcyclopentadienyl)(N-trimethylsilylamino) methylphenylsilane, (trimethylsilylcyclopentadienyl)(tert-butylamino) dimethylsilane, (trimethylsilylcyclopentadienyl)(cyclohexylamino) dimethylsilane, (trimethylsilylcyclopentadienyl) (phenylamino) dimethylsilane, (trimethylsilylcyclopentadienyl)(N-trimethylsilylamino)dimethylsilane, (trimethylsilylcyclopentadienyl)(tert-butylamino) diphenylsilane, (trimethylsilylcyclopentadienyl)(cyclohexylamino) diphenylsilane, (trimethylsilylcyclopentadienyl) (phenylamino) diphenylsilane, (trimethylsilylcyclopentadienyl)(N-trimethylsilylamino)diphenylsilane, (trimethylsilylcyclopentadienyl)(tert-butylamino) methylphenylsilane, (trimethylsilylcyclopentadienyl)(cyclohexylamino)methyl phenylsilane, (trimethylsilylcyclopentadienyl) (phenylamino) methylphenylsilane, (trimethylsilylcyclopentadienyl)(N-trimethylsilylamino)methylphenylsilane, (tert-butyldimethylsilylcyclopentadienyl)(tert-butylamino) dimethylsilane, (tert-butyldimethylsilylcyclopentadienyl)(cyclohexylamino)dimethylsilane, (tert-butyldimethylsilylcyclopentadienyl)(phenylamino) dimethylsilane, (tert-butyldimethylsilylcyclopentadienyl)(N-trimethylsilylamino)dimethylsilane, (tert-butyldimethylsilylcyclopentadienyl)(tert-butylamino) diphenylsilane, (tert-butyldimethylsilylcyclopentadienyl)(cyclohexylamino) diphenylsilane, (tert-butyldimethylsilylcyclopentadienyl)(phenylamino) diphenylsilane, (tert-butyldimethylsilylcyclopentadienyl)(N-trimethylsilylamino)diphenylsilane, (tert-butyldimethylsilylcyclopentadienyl)(tert-butylamino) methylphenylsilane, (tert-butyldimethylsilylcyclopentadienyl)(cyclohexylamino) methylphenylsilane, (tert-butyldimethylsilylcyclopentadienyl)(phenylamino) methylphenylsilane, (tert-butyldimethylsilylcyclopentadienyl)(N-trimethylsilylamino)methylphenylsilane, (1,3-dimethylcyclopentadienyl)(tert-butylamino) dimethylsilane, (1,3-dimethylcyclopentadienyl)(cyclohexylamino) dimethylsilane, (1,3-dimethylcyclopentadienyl) (phenylamino) dimethylsilane, (1,3-dimethylcyclopentadienyl)(N-trimethylsilylamino)dimethylsilane, (1,3-dimethylcyclopentadienyl)(tert-butylamino) diphenylsilane, (1,3-dimethylcyclopentadienyl)(cyclohexylamino) diphenylsilane, (1,3-dimethylcyclopentadienyl) (phenylamino) diphenylsilane, (1,3-dimethylcyclopentadienyl)(N-trimethylsilylamino)diphenylsilane, (1,3- dimethylcyclopentadienyl)(tert-butylamino) methylphenylsilane, (1,3-dimethylcyclopentadienyl) (cyclohexylamino) methylphenylsilane, (1,3-dimethylcyclopentadienyl)(phenylamino) methylphenylsilane, (1,3-dimethylcyclopentadienyl) (N-trimethylsilylamino)methylphenylsilane, (1,3-diisopropylcyclopentadienyl)(tert-butylamino) dimethylsilane, (1,3-diisopropylcyclopentadienyl) (cyclohexylamino) dimethylsilane, (1,3-diisopropylcyclopentadienyl)(phenylamino) dimethylsilane, (1,3-diisopropylcyclopentadienyl)(N-trimethylsilylamino)dimethylsilane, (1,3-diisopropylcyclopentadienyl)(tert-butylamino) diphenylsilane, (1,3-diisopropylcyclopentadienyl) (cyclohexylamino) diphenylsilane, (1,3-diisopropylcyclopentadienyl)(phenylamino) diphenylsilane, (1,3-diisopropylcyclopentadienyl)(N-trimethylsilylamino)diphenylsilane, (1,3-diisopropylcyclopentadienyl)(tert-butylamino) methylphenylsilane, (1,3-diisopropylcyclopentadienyl) (cyclohexylamino) methylphenylsilane, (1,3-diisopropylcyclopentadienyl)(phenylamino) methylphenylsilane, (1,3-diisopropylcyclopentadienyl) (N-trimethylsilylamino)methylphenylsilane, (1,3-di-tert-butylcyclopentadienyl)(tert-butylamino) dimethylsilane, (1,3-di-tert-butylcyclopentadienyl) (cyclohexylamino)dimethylsilane, (1,3-di-tert-butylcyclopentadienyl) (phenylamino)dimethylsilane, (1,3-di-tert-butylcyclopentadienyl)(N-trimethylsilylamino)dimethylsilane, (1,3-di-tert-butylcyclopentadienyl)(tert-butylamino) diphenylsilane, (1,3-di-tert-butylcyclopentadienyl) (cyclohexylamino)diphenylsilane, (1,3-di-tert-butylcyclopentadienyl)(phenylamino)diphenylsilane, (1,3-di-tert-butylcyclopentadienyl)(N-trimethylsilylamino)diphenylsilane, (1,3-di-tert-butylcyclopentadienyl)(tert-butylamino) methylphenylsilane, (1,3-di-tert-butylcyclopentadienyl) (cyclohexylamino) methylphenylsilane, (1,3-di-tert-butylcyclopentadienyl)(phenylamino) methylphenylsilane, (1,3-di-tert-butylcyclopentadienyl)(N-trimethylsilylamino) methylphenylsilane, (1-tert-butylcyclopentadienyl) (tert-butylamino)dimethylsilane, (1-tert-butylcyclopentadienyl)(cyclohexylamino) dimethylsilane, (1-tert-butylcyclopentadienyl) (phenylamino) dimethylsilane, (1-tert-butylcyclopentadienyl)(N-trimethylsilylamino) dimethylsilane, (1-tert-butylcyclopentadienyl)(tert-butylamino)diphenylsilane, (1-tert-butylcyclopentadienyl)(cyclohexylamino) diphenylsilane, (1-tert-butylcyclopentadienyl) (phenylamino)diphenylsilane, (1-tert-butylcyclopentadienyl)(N-trimethylsilylamino) diphenylsilane, (1-tert-butylcyclopentadienyl)(tert-butylamino) methylphenylsilane, (1-tert-butylcyclopentadienyl) (cyclohexylamino) methylphenylsilane, (1-tert-butylcyclopentadienyl) (phenylamino)methylphenylsilane, (1-tert-butylcyclopentadienyl)(N-trimethylsilylamino) methylphenylsilane, (1,2,4-trimethylcyclopentadienyl) (tert-butylamino)dimethylsilane, (1,2,4-trimethylcyclopentadienyl)(cyclohexylamino) dimethylsilane, (1,2,4-trimethylcyclopentadienyl) (phenylamino)dimethylsilane, (1,2,4-trimethylcyclopentadienyl)(N-trimethylsilylamino)

dimethylsilane, (1,2,4-trimethylcyclopentadienyl)(tert-butylamino)diphenylsilane, (1,2,4-trimethylcyclopentadienyl)(cyclohexylamino) diphenylsilane, (1,2,4-trimethylcyclopentadienyl) (phenylamino)diphenylsilane, (1,2,4-trimethylcyclopentadienyl)(N-trimethylsilylamino) diphenylsilane, (1,2,4-trimethylcyclopentadienyl)(tert-butylamino)methylphenylsilane, (1,2,4-trimethylcyclopentadienyl)(cyclohexylamino) methylphenylsilane, (1,2,4-trimethylcyclopentadienyl) (phenylamino)methylphenylsilane, (1,2,4-trimethylcyclopentadienyl)(N-trimethylsilylamino) methylphenylsilane.

Examples also include compounds in which dimethylsilane, diphenylsilane or methylphenylsilane is changed to diethylsilane or dimethoxysilane. In addition, examples further include compounds in which (cyclopentadienyl) in the above specific compounds is changed to (ethylcyclopentadienyl), (n-propylcyclopentadienyl), (sec-butylcyclopentadienyl), (phenylcyclopentadienyl), (naphthylcyclopentadienyl), (triethylsilylcyclopentadienyl), (diethylcyclopentadienyl), (di-n-propylcyclopentadienyl), (di-n-butylcyclopentadienyl), (di-sec-butylcyclopentadienyl), (di-n-pentylcyclopentadienyl), (dineopentylcyclopentadienyl), (di-n-hexylcyclopentadienyl), (di-n-octylcyclopentadienyl), (diphenylcyclopentadienyl), (dinaphthylcyclopentadienyl), (di-(trimethylsilyl)cyclopentadienyl), (di(triethylsilyl) cyclopentadienyl), (di(tert-butyldimethylsilyl) cyclopentadienyl), (triethylcyclopentadienyl), (tri-n-propylcyclopentadienyl), (triisopropylcyclopentadienyl), (tri-n-butylcyclopentadienyl), (tri-sec-butylcyclopentadienyl), (tri-tert-butylcyclopentadienyl), (tri-n-pentylcyclopentadienyl), (trineopentylcyclopentadienyl), (tri-n-hexylcyclopentadienyl), (tri-n-octylcyclopentadienyl), (tri-(trimethylsilyl)-cyclopentadienyl), (tri-(triethylsilyl)-cyclopentadienyl), (tri-(tert-butyldimethylsilyl)-cyclopentadienyl), (indenyl) or (fluorenyl).

In the process of the present invention for producing an aminosilane compound represented by the general formula (1) described above, the following step (A) is carried out. Step (A): a step for reacting a compound having a cyclopentadiene skeleton with a strong base.

The compound having a cyclopentadiene skeleton used in the step (A) is a compound which is made anionic after reacting with the strong base, and become a group having a cyclopentadiene skeleton(Cp) by a subsequent reaction. For example, it is a compound represented by the general formula: Cp-H wherein Cp is a group having a cyclopentadiene skeleton and H is a hydrogen atom.

Specific examples include cyclopentadiene, methylcyclopentadiene, dimethylcyclopentadiene, trimethylcyclopentadiene, tetramethylcyclopentadiene, ethylcyclopentadiene, n-propylcyclopentadiene, isopropylcyclopentadiene, n-butylcyclopentadiene, sec-butylcyclopentadiene, tert-butylcyclopentadiene, n-pentylcyclopentadiene, neopentylbutylcyclopentadiene, n-hexylcyclpoentadiene, n-octylcyclopentadiene, phenylcyclopentadiene, naphthylcyclopentadiene, trimethylsilylcyclopentadiene, triethylsilylcyclopentadiene, tert-butyldi methylsilylcyclopentadiene, indene, 4,5,6,7-tetrahydroindene, fluorene and the like. Preferred examples are tetramethylcyclopentadiene, dimethylcyclopentadiene, di-tert-butylcyclopentadiene, diisopropylcyclopentadiene and isopropyl-tertbutylcyclopentadiene.

Particularly, the present invention is effective when a cyclopentadiene compound having one or more substituents such as alkyl group, substituted silyl group or the like which causes a great increase in volume when the reaction is carried out in an aliphatic solvent, is used, and in particular, effective when, for example, starting from methylcyclopentadiene, tert-butylcyclopentadiene, dimethylcyclopentadiene, di-tert-butylcyclopentadiene, tetramethylcyclopentadiene, or pentamethylcyclopentadiene.

The amount of the compound having a cyclopentadiene skeleton to be used in the step (A) is 1.00 time or more by mole and preferably 1.00–1.50 times by mole to the silane compound represented by the general formula (2) used in the next step (B).

The strong base used in the step (A) is a compound which is capable of making the compound having a cyclopentadiene skeleton anionic, and preferably is an organo-alkali metal compound, an alkali metal hydride or an organomagnesium compound.

The organo-alkali metal compound includes, for example, organo-alkali metal compounds including organo-lithium compounds such as methyl lithium, ethyl lithium, n-butyl lithium, sec-butyl lithium, tert-butyl lithium, lithium trimethylsilylacetylide, lithium acetylide, trimethylsilylmethyl lithium, vinyl lithium, phenyl lithium, allyl lithium and the like, organo-sodium compounds in which lithium in the above compounds is replaced by sodium, organo-potassium compounds in which it is replaced by potassium. Preferred compounds are organo-lithium compounds and more preferred group is alkyl lithium.

The alkali metal hydride includes, for example, sodium hydride, potassium hydride and the like. The organic magnesium compound includes isopropyl magnesium chloride and the like. Preferred strong base used in the step (A) is an organic alkali metal compound.

The amount of the strong base to be used in the step (A) is usually within a range of 0.5 to 5 times by mole, preferably 0.7 to 1.5 times by mole, and more preferably 0.8 to 1.3 times by mole of the compound having a cyclopentadiene skeleton.

If the amount of the strong base is extremely small (for example, less than 0.5 times by mole), the rate of the anion produced from the compound having a cyclopentadiene skeleton decreases, and as the result, the yield of the silane compound in the next step sometimes decreases. If the amount of the strong base is too much (for example, more than 5 times by mole), although a greater amount of the anion is produced, the strong base remains in the system, so that it sometimes reacts with the silane compound resulting in increase of by-product.

Generally, as the organo-alkali metal compound such as butyl lithium is commercialized in the form of a dilution in an aliphatic or aromatic hydrocarbon solvent such as hexane, toluene or the like, the solvent for the organo-alkali metal compound is preferably an aliphatic or aromatic hydrocarbon solvent.

In the step (A), an ethereal solvent is preferably used in view of improvement of reaction yield or the slurry property of the produced salt of the compound having a cyclopentadiene skeleton. In addition, the use of an ethereal solvent is advantageous in carrying out the reaction of the step (A) at a relatively high temperature because the stability and the production efficiency of said salt compound are increased at a relatively high temperature.

Therefore, a preferred solvent for the compound having a cyclopentadiene skeleton is an ethereal solvent.

The ethereal solvent includes, for example, tetrahydrofuran, dioxane, diethyl ether, diisopropyl ether, di-n-butyl ether, diisobutyl ether and the like, amongst which tetrahydrofuran is preferably used.

In the step (A), when a mixture of an ethereal solvent and other solvent (e.g. an aliphatic or aromatic hydrocarbon solvent) is used, it is preferred that the proportion of the ethereal solvent in the total amount of the mixed solvent is 50% by volume or more.

The reaction in the step (A) is preferably carried out at a temperature of −20° C. or higher, at which the limitation to the apparatus used in industrial operation is small, more preferably −20 to 50° C., and most preferably at −20 to 30° C.

It is preferred that the reaction in the step (A) is started at a relatively low temperature and completed at a subsequently elevated temperature. Since the reaction in the step (A) proceeds particularly efficiently, it is effective that the reactants are contacted at −20 to 10° C., without elevating immediately the temperature, the system is kept at the temperature and stirred for a predetermined period, and then the temperature is elevated to 10° C. or higher. This manner allows to suppress the formation of by-product and advance to the next reaction with a good efficiency.

In the process for producing an aminosilane compound represented by the general formula (1), the following step (B) is carried out after the step (A), without an intervening isolation nor purification treatment. Step (B) is a step for reacting the reaction product obtained in the step (A) with a silane compound represented by the general formula (2); and

(2)

wherein $R^3$, $R^4$, $X^1$ and $X^2$ are the same as those described above.

While, in the present invention, the above step (B) is carried out without an intervening isolation nor purification treatment after the step (A), treatments such as concentration under reduced pressure, heating or the like, or the like may be inserted.

In the silane compound represented by the general formula (2) described above, specific examples of $R^3$ and $R^4$ are the same as those described above in the general formula (1).

In the general formula (2) described above, $X^1$ and $X^2$ independently represent a halogen atom. Examples of the halogen atom include fluorine atom, chlorine atom, bromine atom and iodine atom, among them, chlorine atom and bromine atom are preferred and chlorine atom is more preferred.

Specific examples of the silane compound represented by the general formula (2) described above include dichlorodimethylsilane, dichlorodiphenylsilane, dichlorodiethylsilane, dichlorodi-n-propylsilane, dichlorodimethoxylsilane, diallyldichlorosilane, dichlorodivinylsilane, dichloromethylvinylsilane, dichlorodibenzylsilane, dichlorochloromethylmethylsilane, dibromodimethylsilane, diiododimethylsilane and the like.

The step (B) may be conducted by adding dropwise the reaction product obtained in the step (A) to the silane compound represented by the general formula (2) while stirring, or by adding dropwise the silane compound represented by the general formula (2) to the reaction product obtained in the step (A).

The reaction is generally conducted in an inert solvent. More specifically, it is generally carried out in an aromatic hydrocarbon solvent such as benzene, toluene, mesitylene or the like; an aliphatic hydrocarbon solvent such as pentane, hexane, heptane or the like; or an ethereal solvent such as tetrahydrofuran, dioxane, diethyl ether, diisopropyl ether, di-n-butyl ether, diisobutyl ether or the like.

In the step (B), the solvent for the reaction product obtained in the step (A) is usually a mixture of solvents for respective reactants used in the step (A). On the other hand, a solvent for the silane compound described above is not particularly limited and preferably an ethereal solvent, an aliphatic hydrocarbon solvent or an aromatic hydrocarbon solvent as described above.

When a mixed solvent of an ethereal solvent with an aromatic or aliphatic hydrocarbon solvent is used in the step (A) and an ethereal solvent is used as the solvent for the silane compound used in the step (B), the reaction result sometimes depends on the proportion of respective solvents in the mixed solvent. Therefore, it is preferred that the proportion of the ethereal solvent occupied in the total solvent used is 70% by volume or more. More preferably, the proportion of the ethereal solvent is 80 to 99% by volume. There is a tendency that the reaction rate increases with the increasing proportion of the ethereal solvent, and sometimes the degree of conversion is also improved. In addition, the use of the mixed solvent of high content of the ethereal solvent is preferable since stirring efficiency, volume efficiency and operability are good due to improvement of the slurry property.

The reaction temperature of the step (B) is preferably −20° C. or higher, at which the limitation to the apparatus used in industrial operation is relatively small, more preferably −20 to 100° C., and most preferably −10 to 100° C. When an ethereal solvent is used in the step (A), the step (B) is particularly preferably carried out at a temperature of 0 to 50° C. because the stability and reactivity of the salt compound of the compound having a cyclopentadiene skeleton produced in the step (A) are particularly excellent.

In the process for producing an aminosilane compound represented by the general formula (1), the following step (C) is carried out without an intervenient isolation nor purification treatment after the step (B). Step (C) is a step for reacting the reaction product obtained in the step (B) with an amine compound represented by the general formula (3) or an alkali metal amide compound represented by the general formula (4):

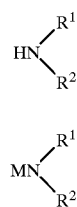

wherein, M, $R^1$ and $R^2$ are the same as those described above.

While, in the present invention, the above step (C) is carried out without an intervening purification treatment after carrying out the step (B), treatments such as concentration under reduced pressure, heating or the like, or the like may be inserted.

In the amine compound represented by the general formula (3) described above, $R^1$ and $R^2$ independently preferably represent a hydrogen atom, an alkyl group, an aralkyl group, an aryl group or a substituted silyl group. Specific examples of $R^1$ and $R^2$ are the same as those described above in the general formula (1).

Specific examples of the amine compound represented by the general formula (3) preferably used includes primary amine compounds such as methylamine, ethylamine, n-propylamine, isopropylamine, n-butylamine, tert-butylamine, cyclohexylamine, n-octylamine, n-decylamine, aniline, ethylenediamine and the like; and secondary amine compounds such as dimethylamine, diethylamine, di-n-propylamine, diisopropylamine, di-n-butylamine, di-tert-butylamine, di-n-octylamine, di-n-decylamine, pyrrolidine, hexamethyldisilazane, diphenylamine and the like. The amine compound used in the present invention is more preferably a primary amine compound.

In the alkali metal amide compound represented by the general formula (4) described above, M is an alkali metal atom; $R^1$ and $R^2$ are independent from each other and represent a hydrogen atom, an alkyl group, an aralkyl group, an aryl group or a substituted silyl group. $R^1$ and $R^2$ are the same as those described above in the general formula (1).

M in the general formula (4) specifically includes lithium, sodium and potassium.

The alkali metal amide compound represented by the general formula (4) may be one prepared by premixing the amine compound of the general formula (3) with an organo-alkali metal compound or an alkali metal hydride before conducting the step (C).

The amount used of the amine compound represented by the general formula (3) in the step (C) is usually 1.0 equivalent or more, preferably 1.5 equivalent or more, based on the silane compound of the general formula (2) used in the preceding step (B). Since, in the reaction of the silane compound and the amine compound, the formation of an ammonium salt compound as by-product is observed in the system, it is also preferred to conduct the reaction in the presence of an tertiary amine compound such as triethylamine in addition to the amine compound of the general formula (3). More preferred amount of the amine compound of the general formula (3) is 2 to 10 equivalents based on the silane compound used in the step (B), taking into consideration loss by the formation of the ammonium salt compound.

The amount of the alkali metal amide compound represented by the general formula (4) used in the step (C) is usually 0.8 equivalent or more, preferably 1.0 equivalent or more, based on the silane compound of the general formula (2) used in the preceding step (B). While this reaction proceeds rapidly as compared to the reaction using the amine compound of the general formula (3), the reaction with the silane compound produced in the preceding step (B) is not sufficient if the amount is smaller and, as the result, the yield decreases. On the other hand, if the amount is in the great excess, the post treatment for removing the remaining alkali metal amide compound is troublesome. Therefore, the amount of the alkali metal amide compound is more preferably 1.1 to 3 equivalents based on the silane compound of the general formula (2) used in the preceding step (B).

The reaction is generally conducted in an inert solvent. Generally, it is usually carried out in an ethereal solvent such as tetrahydrofuran, dioxane, diethyl ether, diisopropyl ether, di-n-butyl ether, diisobutyl ether or the like. From the viewpoint that the reaction is carried out without an intervening isolation nor purification treatment from the step (A) to the step (C) and with least replacement of solvent, the solvent for the reaction product obtained in the step (B) is usually a mixture of solvents for the reactant used in the steps (A) and (B). On the other hand, a solvent for the amine compound represented by the general formula (3) described above or the alkali metal amide compound represented by the general formula (4) described above is not particularly limited and preferably an ethereal solvent such as tetrahydrofuran, dioxane, diethyl ether, diisopropyl ether, di-n-butyl ether, diisobutyl ether or the like, an aromatic hydrocarbon solvent such as toluene or the like, or an aliphatic hydrocarbon solvent such as hexane or the like. Preferred proportion of solvents is the same as that described for the step (B).

The reaction in the step (C) is preferably carried out at a temperature of −20° C., more preferably −20 to 120° C., most preferably at −10 to 100° C. Particularly, when the reaction is conducted between the reaction product obtained in the step (B) and the amine compound of the formula (3), a higher temperature is required in order to improve the reaction yield, as compared with the reaction using the alkali metal amide compound of the general formula (4). In this case, it is preferred to conduct the reaction at 20 to 80° C. On the other hand, when the alkali metal amide compound of the general formula (4) is used, it is preferred to conduct the reaction at −10 to 60° C., since the reaction rate is relatively rapid as compared with the case in which the amine compound is used.

EXAMPLE

The present invention will be explained in more detail below by reference of Examples, but is not limited thereto.

Example 1(1)
Synthesis of (tetramethylcyclopentadienyl) dimethylchlorosilane Into a two-necked round-bottomed flask, the atmosphere in which was replaced with nitrogen, were charged 30 g of tetrahydrofuran and 1.10 g of tetramethylcyclopentadiene. The mixture was cooled to 0° C. with stirring and 4.90 ml of n-butyl lithium (1.6M solution in n-hexane) (7.84 mmol as n-butyl lithium) was gradually added dropwise thereto over 20 minutes. The obtained reaction mixture in the form of a white slurry was stirred further for at 0° C. for 3 hours, and added to a pre-cooled tetrahydrofuran (20 g) solution containing 1.01 g (7.84 mmol) of dichlorodimethylsilane in several divided portions over 15 minutes. The mixture was then gradually warmed to room temperature.

After the stirring of the above reaction solution at room temperature for 2 hours, the obtained reaction solution was analyzed by means of gas chromatography. The main product was (tetramethylcyclopentadienyl) dimethylchlorosilane, and the content of it in the product having a higher boiling point than tetramethylcyclopentadiene was 98%.

Example 1(2)
Synthesis of (tetramethylcyclopentadienyl)(tert-butylamino) dimethylsilane Into the reaction solution, pre-cooled to 0° C., containing (tetramethylcyclopentadienyl) dimethylchlorosilane obtained in Example 1(1) described above was rapidly added 1.5 g of lithium tert-butyl amide (LiNH-tert-Bu). Themixturewas kept at 0° C. for 30minutes, then gradually heated to room temperature and further stirred at room temperature for 3 hours.

After completion of the reaction, the obtained reaction solution was analyzed by means of gas chromatography. As the result, it was revealed that the desired product (tetramethylcyclopentadienyl)(tert-butylamino) dimethylsilane was formed in 88% yield. The contaminated main impurity was (tetramethylcyclopentadienyl) dimethylchlorosilane alone, and the amount of by-products having a higher boiling point was very small.

Example 2 (1)
Synthesis of (tetramethylcyclopentadienyl) dimethylchlorosilane Into a two-necked round-bottomed flask, the atmosphere in which was replaced with nitrogen, were charged 30 g of tetrahydrofuran and 1.10 g of tetramethylcyclopentadiene. The mixture was cooled to 0° C. with stirring and 4.90 ml of n-butyl lithium (1.6M solution in n-hexane) (7.84 mmol as n-butyl lithium) was gradually added dropwise thereto over 20 minutes. The obtained reaction mixture in the form of a white slurry was stirred further for at 0° C. for 3 hours, and added to a pre-cooled mixed solution of tetrahydrofuran (10 g) and n-hexane (10 g) containing 1.01 g (7.84 mmol) of dichlorodimethylsilane in several divided portions over 15 minutes. The mixture was then gradually heated to room temperature.

After the stirring of the above reaction solution at room temperature for 2 hours, the obtained reaction solution was analyzed by means of gas chromatography, upon which it was shown that the main component was (tetramethylcyclopentadienyl)dimethylchlorosilane, and that the content of the main component in the products having a higher boiling point than tetramethylcyclopentadiene was 98%.

Example 2 (2)
Synthesis of (tetramethylcyclopentadienyl)(tert-butylamino) dimethylsilane Into the reaction solution, pre-cooled to 0° C., containing (tetramethylcyclopentadienyl) dimethylchlorosilane obtained in Example 2 (1) described above was rapidly added 1.5 g of lithium tert-butyl amide (LiNH-tert-Bu). The mixture was kept at 0° C. for 30minutes, then gradually heated to room temperature and further stirred at room temperature for 2 hours and at 50° C. for 3 hours.

After completion of the reaction, the obtained reaction solution was concentrated under reduced pressure, and extracted with cooled hexane. Again, hexane was evaporated to give 2.2 g of thick yellow liquid. The reaction product was analyzed by means of gas chromatography, upon which it was revealed that the desired product (tetramethylcyclopentadienyl)(tert-butylamino) dimethylsilane was contained in 83% yield. The rate of conversion of (tetramethylpentadienyl)dimethylchlorosilane was 94%, and the overall yield from dichlorodimethylsilane and butyl lithium used was 92%.

Example 3 (1)
Synthesis of (tetramethylcyclopentadienyl) dimethylchlorosilane Into a two-necked round-bottomed flask, the atmosphere in which was replaced with nitrogen, were charged 15 g of tetrahydrofuran, 12 g of n-hexane and 1.10 g of tetramethylcyclopentadiene. The mixture was cooled to 0° C. with stirring and 4.90 ml of n-butyl lithium (1.6M solution in n-hexane) (7.84 mmol as n-butyl lithium) was gradually added dropwise thereto over 20 minutes. The obtained reaction mixture in the form of a white slurry was stirred for at 0° C. for 3 hours, and a pre-cooled tetrahydrofuran (10 g) solution containing 1.01 g (7.84 mmol) of dichlorodimethylsilane was added in several divided portions. The mixture was then gradually heated to room temperature.

After the stirring of the above reaction solution at room temperature for 14 hours, the obtained reaction solution was analyzed by means of gas chromatography, upon which it was shown that the main product was (tetramethylcyclopentadienyl)dimethylchlorosilane, and that the content of the main product in the products having a higher boiling point than tetramethylcyclopentadiene was more than 99% by weight.

Example 3 (2)

Synthesis of (tetramethylcyclopentadienyl)(tert-butylamino) dimethylsilane

Into the reaction solution, pre-cooled to 0° C., containing (tetramethylcyclopentadienyl) dimethylchlorosilane obtained in Example 3 (1) was rapidly added 1.5 g of lithium tert-butyl amide (LiNH-tert-Bu). The mixture was kept at 0° C. for 30 minutes, then gradually heated to room temperature and further stirred at room temperature for 3 hours and at 50° C. for additional 6 hours.

After completion of the reaction, the obtained reaction solution was analyzed by means of gas chromatography, upon which it was revealed that the desired product [(tetramethylcyclopentadienyl)(tert-butylamino) dimethylsilane] was formed. The main product was (tetramethylcyclopentadienyl)(tert-butylamino) dimethylsilane. The weight ratio of the product [(tetramethylcyclopentadienyl)(tert-butylamino) dimethylsilane] to the total of the product and the material for reaction [(tetramethylcyclopentadienyl) dimethylchlorosilane] [product/(product+material)] was 0.88.

Example 4 (1)

Synthesis of (tetramethylcyclopentadienyl) dimethylchlorosilane

Into a two-necked round-bottomed flask, the atmosphere in which was replaced with nitrogen, were charged 15 g of tetrahydrofuran, 12 g of n-hexane and 1.10 g of tetramethylcyclopentadiene. The mixture was cooled to 0° C. with stirring and 4.90 ml of n-butyl lithium (1.6 M solution in n-hexane) (7.84 mmol as n-butyl lithium) was gradually added dropwise thereto over 20 minutes. The obtained reaction mixture in the form of a white slurry was stirred further for at 0° C. for 3 hours, and a pre-cooled mixed solution of tetrahydrofuran (10 g) and n-hexane (10 g) containing 1.01 g (7.84 mmol) of dichlorodimethylsilane was added in several divided portions. The mixture was then gradually heated to room temperature.

After the stirring of the above reaction solution at room temperature for 14 hours, the obtained reaction solution was analyzed by means of gas chromatography, upon which it was shown that the main product was (tetramethylcyclopentadienyl)dimethylchlorosilane, and that the content of the main product in the products having a higher boiling point than tetramethylcyclopentadiene was 99% by weight.

Example 4 (2)

Synthesis of (tetramethylcyclopentadienyl)(tert-butylamino) dimethylsilane

Into the reaction solution, pre-cooled to 0° C., containing (tetramethylcyclopentadienyl)dimethylchlorosilane obtained in Example 4 (1) was rapidly added 1.5 g of lithium cyclohexyl amide (LiNH(cyclo-$C_6H_{11}$)). The mixture was kept at 0° C. for 30 minutes, then gradually heated to room temperature and further stirred at room temperature for 2 hours and at 50° C. for 3 hours.

After the reaction was over, the obtained reaction solution was analyzed by means of gas chromatography, upon which it was revealed that the desired product (tetramethylcyclopentadienyl)(tert-butylamino) dimethylsilane was formed in 87% yield. The rate of conversion of (tetramethylcyclopentadienyl) dimethylchlorosilane was 92%.

The present invention provides a process for producing aminosilane compounds which are useful as precursors for ligands in the transition metal complexes, said process avoiding handling of solid which is troublesome in isolation and purification and combustible upon contact with air, having smaller number of reaction steps, and giving a high yield, in industrial scale. The present invention has a great value that said process for production could be carried out at an industrially advantageous temperature of −20° C. or higher.

What is claimed is:

1. A process for producing an aminosilane compound represented by the general formula (1) described below, which comprises carrying out steps (A), (B) and (C) in this order without an intervenient isolation nor purification treatment:

(A): reacting a compound having a cyclopentadiene skeleton with a strong base;
   (B): reacting the reaction product obtained in the step (A) with a silane compound represented by the general formula (2); and
   (C): reacting the reaction product obtained in the step (B) with an amine compound represented by the general formula (3) or an alkali metal amide compound represented by the general formula (4);

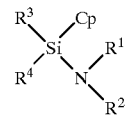
(1)

(2)

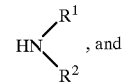
(3)

(4)

wherein, for the respective general formulae (1), (2), (3) and (4), Cp represents a group having a cyclopentadiene skeleton; M represents an alkali metal atom; $R^1$ and $R^2$ independently represent a hydrogen atom, an alkyl group, an aralkyl group, an aryl group or a substituted silyl group; $R^3$ and $R^4$ independently represent an alkyl group, an aralkyl group, an aryl group, a substituted silyl group, an alkoxy group, an aralkyloxy group or an aryloxy group; ($R^1$ and $R^2$) and/or ($R^3$ and $R^4$) may be linked to form a ring; and $X^1$ and $X^2$ independently represent a halogen atom.

2. A process for producing an aminosilane compound according to claim 1, wherein each of the steps (A), (B) and (C) is carried out at a temperature of −20° C. or higher.

3. A process for producing an aminosilane compound according to claim 1, wherein the compound having a cyclopentadiene skeleton is used in the form of a solution in an ethereal solvent.

4. A process for producing an aminosilane compound according to claim 1, wherein the strong base is used in the form of a solution in an aliphatic or aromatic hydrocarbon solvent.

5. A process for producing an aminosilane compound according to claim 1, wherein the strong base is an organoalkali metal compound.

6. A process for producing an aminosilane compound according to claim 1, wherein the Cp is a group having a cyclopentadiene skeleton containing at least one substituent on its five-membered ring.

7. A process for producing an aminosilane compound according to claim 1, wherein Cp is a member selected from the group consisting of a tetramethylcyclopentadienyl group, a dimethylcyclopentadienyl group, a di-tert-butylcyclopentadienyl group, a diisopropylcyclopentadienyl group and an isopropyl-tert-butylcyclopentadienyl group.

8. A process for producing an aminosilane compound according to claim 1, wherein one of $R^1$ and $R^2$ is a hydrogen atom and the other is an alkyl group or a substituted silyl group.

9. A process for producing an aminosilane compound according to claim 1, wherein M in the general formula (4) is a lithium atom.

10. A process for producing an aminosilane compound according to claim 1, wherein the reaction in the step (A) is carried out at a temperature of $-20$ to $30°$ C.

11. A process for producing an aminosilane compound according to claim 1, wherein both reactions in the steps (B) and (C) are carried out at a temperature of $-10$ to $100°$ C.

* * * * *